US006544779B1

(12) United States Patent
Cichutek et al.

(10) Patent No.: US 6,544,779 B1
(45) Date of Patent: Apr. 8, 2003

(54) PSEUDO-TYPE RETROVIRAL VECTORS WITH MODIFIABLE SURFACE CAPSID PROTEINS

(75) Inventors: Klaus Cichutek, Langen (DE); Heike Merget-Millitzer, Soligenstadt (DE)

(73) Assignee: Bundesrepublik Deutschland, Langen (DE)

( * ) Notice: Subject to any disclaimer, the term of this patent is extended or adjusted under 35 U.S.C. 154(b) by 0 days.

(21) Appl. No.: 09/555,352

(22) PCT Filed: Nov. 27, 1998

(86) PCT No.: PCT/DE98/03542

§ 371 (c)(1),
(2), (4) Date: Aug. 24, 2000

(87) PCT Pub. No.: WO99/28488

PCT Pub. Date: Jun. 10, 1999

(30) Foreign Application Priority Data

Nov. 28, 1997 (DE) ........................................ 197 52 855

(51) Int. Cl.$^7$ ........................ C12N 15/83; C12N 15/85; C12N 15/86; C12N 15/867; A61K 39/12

(52) U.S. Cl. .................. 435/320.1; 435/69.1; 424/93.2; 424/199.1; 424/265.1; 424/208.1; 530/387.3

(58) Field of Search ............................ 435/320.1, 69.1, 435/235.1; 530/387.3; 424/93.2, 199.1, 205.1, 208.1

(56) References Cited

U.S. PATENT DOCUMENTS 5,869,331 A * 2/1999 Dornburg et al. ........ 435/320.1

FOREIGN PATENT DOCUMENTS

| | | |
|---|---|---|
| WO | WO 95/23846 | 8/1995 |
| WO | WO 96/30504 | 3/1996 |

OTHER PUBLICATIONS

Orkin et al. Report and recommendations of the panel to assess the NIH inventment in research on gene therapy, 1995.*

Verma, Nature 1997, vol. 389, pp. 239–242.*

Friedmann et al. Nature medicine 1995, vol. 1, pp. 275–277.*

Takeuchi et al. Virology, 1992, vol. 186, pp. 792–794.*

W. French Anderson Nature, 1996, vol. 392, pp. 25–30.*

Anderson, "Human Gene Therapy" *Science* 256:808–813, 1992.

Buchschacher et al., "Human Immunodeficiency Virus Vectors for Inducible Expression of Foreign Genes" *J. Virol.*, 66:2731–2739, 1992.

Burns et al., "*Vesicular stomatitis* virus G glycoprotein pseudotyped retroviral vectors: Concentration to very high titer and efficient gene transfer into mammalian and non-mammalian cells" *Proc. Natl. Acad. Sci USA*, 90:8033–8037, 1993.

Chu et al., "Toward Highly Efficient Cell–Type–Specific Gene Transfer with Retroviral Vectors Displaying Single–chain Antibodies" *J. Virol.* 71:720–725, 1997.

Cosset et al., "Retroviral Retargeting by Envelopes Expressing an N–Terminal Binding Domain" *J. Virol.*, 69:6314–6322, 1995.

Huston et al., "Protein Engineering of single–chain Fv Analogs and Fusion Proteins" *Methods Enzymol.*, 203:46–88.

Kasahara et al., "Tissue–Specific Targeting of Retroviral Vectors Through Ligand–Receptor Interactions" *Science*, 266:1373–1375, 1994.

Mammano et al., "Truncation of the Human Immunodeficiency Virus Type 1 Envelope Glycoprotein Allow Efficient Pseudotyping of Moloney Murine Leukemia Virus Particles and Gene Transfer into $CD4^+$Cells" *J. Virol*, 71:3341–3345, 1997.

Morgan et al., "Analysis of the Functional and Host Range –Determining Regions of the Murine Ecotropic and Amphotropic Retrovirus Envelope Proteins" *J. Virol.*, 67:4712–4721, 1993.

Naldini et al., "In Vivo Gene Delivery and Stable Transduction of Nondividing Cells by a Lentiviral Vector" *Science*, 272:263–267, 1996.

Poeschla et al., "Development of HIV vectors for anti–HIV gene therapy" *Proc. Natl. Acad. Sci USA*, 93:11395–11399, 1996.

Porter et al., "Comparison of Efficiency of Infection of Human Gene Therapy Target Cells via Four Different Retroviral Receptors" *Hum Gene Ther.* 7:913–919, 1996.

Reiser et al., "Transduction of nondividing cells using pseudotyped defective high–tier HIV type 1 particles" *Proc. Natl. Acad. Sci. USA*, 93:15266–15271, 1996.

Russel et al., "Retroviral vectors displaying functional antibody fragments" *Nucl. Acids Res.* 21:1081–1085, 1993.

Schnierle et al., "Pseudotyping of murine leukemia virus with the envelope glycoproteins of HIV generates a retroviral vector with specificity of infection for CD4–expressing cells" *Proc. Natl. Acad. Sci. USA*, 94:8640–8645, 1997.

Somia et al., "Generation of targeted retroviral vectors by using single–chain variable fragment: An approach to in vivo gene delivery" *Proc. Natl. Acad. Sci. USA*, 92:7570–7574, 1995.

Takeuschi et al., "Type C Retrovirus Inactivation by Human complement is Determined by both the Viral Genome and the Producer Cell" *J. Virol.*, 68:8001–8007, 1994.

(List continued on next page.)

*Primary Examiner*—James Housel
*Assistant Examiner*—Bao Qun Li
(74) *Attorney, Agent, or Firm*—Fish & Richardson P.C.

(57) ABSTRACT

The invention relates to pseudo-typed retroviral vectors having modified surface capsid proteins suitable for cell-specific transduction of a selected mammalian cell type (cell targeting), methods for the preparation of the cell-specific pseudo-typed retroviral vectors and to their use in gene transfer into selected cells.

11 Claims, 7 Drawing Sheets

OTHER PUBLICATIONS

Takeuschi et al., "Retroviral Pseudotypes Produced by Rescue of a Moloney Murine Leukemia Virus Vector by C–type, but not D–type, Retroviruses" *Virology*, 186:792–794, 1992.

Valsesia–Wittmann et al., "Improvement of Retroviral Retargeting by Using Amino Acid Spacers between an Additional Binding Domain and the N Terminus of Moloney Murine Leukemia Virus SU" *J. Virol.*, 70:2059–2064, 1996.

Vile et al., "A Murine Cell Line Producing HTLV–I Pseudotype Virions Carrying a Selectable Marker Gene" *Virology* 186:420–424, 1991.

* cited by examiner pTC53.SEQ [1 to 4776] -> Genes

DNA sequence 4776 b.p. GAATTCCCGTAC ... ACGACGGCCAGT linear

```
   1 GAATTCCCGTACGAGCCATAGATAAAATAAAAGATTTTATTTAGTCTCCAGAAAAAGGGGGA ATG AAA GAC CCC ACC TGT AGG TTT GGC  90
   1                                                                M   K   D   P   T   C   R   F   G    9

  91 AAG CTA GCT TAA GTAACGCCATTTTGCAAGGC ATG GAA AAA TAC ATA ACT GAG AAT AGA GAA GTT CAG ATC AAG GTC AGG 170
  10 K   L   A   *                        M   E   K   Y   I   T   E   N   R   E   V   Q   I   K   V   R    16

 171 AAC AGA TGG AAC AGC TGA AT ATG GGC CAA ACA GGA TAT CTG TGG TAA GCAGTTCCTGCCCCGGCTCAGGGCCAAGAACAG ATG 253
  17 N   R   W   N   S   *      M   G   Q   T   G   Y   L   W   *                                     M     1

 254 GAA CAG CTG AAT ATG GGC CAA ACA GGA TAT CTG TGG TAA GCAGTTCCTGCCCCGGCTCAGGGCCAAGAACAG ATG GTC CCC     334
   2 E   Q   L   N   M   G   Q   T   G   Y   L   W   *                                     M   V   P       3

 335 AGA TGC GGT CCA GCC CTC AGC AGT TTC TAG AGAACCATCAG ATG TTT CCA GGG TGC CCC AAG GAC CTG AAA TGA CCCT 412
   4 R   C   G   P   A   L   S   S   F   *               M   F   P   G   C   P   K   D   L   K   *         11

 413 GTGCCTTATTTGAACTAACCAATCAGTTCGCTTCTCGCTTCTGTTCGCGCGCTTCTGCTCCCCGAGCTCAATAAAAGAGCCCACAACCCCTCACTCGGGG 512

 513 CGCCAGTCCTCCGATTGACTGAGTCGCCCGGGTGGGGGAGCTCGCTGTTGGGCTCGCGGTTGAGGACAAACTCTTCGCGGTCTTTCCAGTACTCTTGGAT 612

 613 CGGAAACCCGTCGGCCTCCGAACGGTACTCCGCCACCGAGGGACCTGAGCGAGTCCGCATCGACCGGATCGGAAAACCTCTCGAGAAAGGCGTCTAACCA 712

 713 GTCACAGTCGCAAGGTAGGCTGAGCACCGTGGCCGGGCGGCACGGGTGGCGGTCGGGGTTGTTTCTGGCGGAGGTGCTGCTG ATG ATG TAA TTAAG 808
   1                                                                                   M   M   *           3

 809 TAGGCGGTCTTGAGACGGCG ATG GTC GAG GTG AGG TGT GGC AGG CTT GAG ATC TGG CCA TAC ACT TGA GTGACA ATG ACA  888
   1                      M   V   E   V   R   C   G   R   L   E   I   W   P   Y   T   *          M   T      2

 889 TCC ACT TTG CCT TTC TCT CCA CAG GTG TCC ACT CCC AGG TCC AAC CGG ATC CGA GCT CCA CCG CGG TAA AGGTCGCT 965
   3 S   T   L   P   F   S   P   Q   V   S   T   P   R   S   N   R   I   R   A   P   P   R   *            25

 966 GGGAAGACCCCGTGGATCCACCACTCTCGACTCAAGAAAGCTCCTGACAACCAAGAAGA ATG GAC TGT CTC ACC AAC CTC CGA TCC GCT 1054
   1                                                             M   D   C   L   T   N   L   R   S   A     10

1055 GAG GGT AAA GTT GAC CAG GCG AGC AAA ATC CTA ATT CTC CTT GTG GCT TGG TGG GGG TTT GGG ACC ACT GCC GAA 1129
  11 E   G   K   V   D   Q   A   S   K   I   L   I   L   L   V   A   W   W   G   F   G   T   T   A   E     35

1130 GTT TCG ACT GCC GGC TCC GGG GGC GGT GGT TCT GGT GGT GGT TCT GGT GGT GGT GGT TCT GGT GGT GGT GGT TCT 1204
  36 V   S   T   A   G   S   G   G   G   G   S   G   G   G   S   G   G   G   G   S   G   G   G   G   S     60
```

FIG. 4A-1

1205 GGC GCC AGC CCA GTC CAG TTT ATC CCC CTG CTT GTG GGT CTA GGG ATT TCA GGG GCT ACA CTT GCT GGT GGA ACG 1279
61 G A S P V Q F I P L L V G L G I S G A T L A G G T 85

1280 GGG CTT GGG GTC TCC GTT CAC ACT TAT CAC AAG CTC TCT AAT CAA TTG ATT GAA GAT GTC CAG GCT CTT TCA GGG 1354
86 G L G V S V H T Y H K L S N Q L I E D V Q A L S G 110

1355 ACC ATC AAT GAC CTA CAG GAC CAG ATT GAC TCC CTG GCT GAG GTT GTC TTA CAA AAT AGA AGA GGG TTA GAC CTA 1429
111 T I N D L Q D Q I D S L A E V V L Q N R R G L D L 135

1430 TTG ACT GCC GAA CAA GGA GGA ATA TGT CTC GCA CTC CAG GAG AAG TGT TGT TTT TAC GCT AAC AAG TCG GGT ATC 1504
136 L T A E Q G G I C L A L Q E K C C F Y A N K S G I 160

1505 GTA CGT GAC AAG ATC CGA AAA CTC CAA GAG GAC CTT ATC GAG AGA AAA CGT GCA CTG TAC GAC AAC CCC CTG TGG 1579
161 V R D K I R K L Q E D L I E R K R A L Y D N P L W 185

1580 AGC GGC TTG AAC GGC TTC CTT CCA TAT TTG CTA CCC TTG TTA GGC CCC CTG TTT GGG CTC ATA TTG TTC CTG ACC 1654
186 S G L N G F L P Y L L P L L G P L F G L I L F L T 210

1655 CTC GGC CCG TGC ATT ATG AAG ACC CTG ACT CGC ATT ATA CAT GAC AAA ATT CAG GCA GTA AAA TCC TAG CACTAGTC 1731
211 L G P C I M K T L T R I I H D K I Q A V K S * 233

1732 CCACAGTACAAGCCACTCCCAACAGAG ATG GAT ACC CTA GGG GTC CGA TGG TCT AAG AAT TCT CGA GTC TAA GATCGATCGAAT 1815
1 M D T L G V R W S K N S R V * 15

1816 TCCTAGGTCA ATG ATT TGA CCAGA ATG TAC AAG AGC AGT GGG GAA TGT GGG AGG GGC TTA CGA AGG CCT TAA GTGACTA 1894
1 M I * M Y K S S G E C G R G L R R P * 16

1895 GGTACCCGATCCAGAC ATG ATA AGA TAC ATT GAT GAG TTT GGA CAA ACC ACA ACT AGA ATG CAG TGA AAAAA ATG CTT 1972
1 M I R Y I D E F G Q T T T R M Q * M L 2

1973 TAT TTG TGA AATTTGTG ATG CTA TTG CTT TAT TTG TAA CCATTATAAGCTGCAATAAACAAGTTAACAACAACAATTGCATTCATTTT 2060
3 Y L * M L L L Y L * 7

2061 ATG TTT CAG GTT CAG GGG GAG GTG TGG GAG GTT TTT TAA AGCAAGTAAAACCTCTACAAATCAAGCTGGGCAAGCTAGATCTAGCTT 2147
1 M F Q V Q G E V W E V F * 13

2148 GGCGTAATC ATG GTC ATA GCT GTT TCC TGT GTG AAA TTG TTA TCC GCT CAC AAT TCC ACA CAA CAT ACG AGC CGG 2222
1 M V I A V S C V K L L S A H N S T Q H T S R 22

2223 AAG CAT AAA GTG TAA AGCCTGGGGTGCCTA ATG AGT GAG CTA ACT CAC ATT AAT TGC GTT GCG CTC ACT GCC CGC TTT 2300
23 K H K V * M S E L T H I N C V A L T A R F 16

FIG. 4A-2

2301 CCA GTC GGG AAA CCT GTC GTG CCA GCT GCA TTA ATG AAT CGG CCA ACG CGC GGG GAG AGG CGG TTT GCG TAT TGG 2375
17 P V G K P V V P A A L M N R P T R G E R R F A Y W 41

2376 GCG CTC TTC CGC TTC CTC GCT CAC TGA CTCGCTGCGCTCGGTCGTTCGGCTGCGGCGAGCGGTATCAGCTCACTCAAAGGCGGTAATACGG 2466
42 A L F R F L A H * 50

2467 TTATCCACAGAATCAGGGGATAACGCAGGAAAGAAC ATG TGA GCAAAAGGCCAGCAAAAGGCCAGGAACCGTAAAAAGGCCGCGTTGCTGGCGTTTT 2563
1 M * 2

2564 TCCATAGGCTCCGCCCCCCTGACGAGCATCACAAAAATCGACGCTCAAGTCAGAGGTGGCGAAACCCGACAGGACTATAAAGATACCAGGCGTTTCCCCC 2663

2664 TGGAAGCTCCCTCGTGCGCTCTCCTGTTCCGACCCTGCCGCTTACCGGATACCTGTCCGCCTTTCTCCCTTCGGGAAGCGTGGCGCTTTCTCA ATG 2759
1 M 1

2760 CTC ACG CTG TAG GTATCTCAGTTCGGTGTAGGTCGTTCGCTCCAAGCTGGGCTGTGTGCACGAACCCCCCGTTCAGCCCGACCGCTGCGCCTTATC 2855
2 L T L * 5

2856 CGGTAACTATCGTCTTGAGTCCAACCCGGTAAGACACGACTTATCGCCACTGGCAGCAGCCACTGGTAACAGGATTAGCAGAGCGAGGT ATG TAG GC 2952
1 M * 2

2953 GGTGCTACAGAGTTCTTGAAGTGGTGGCCTAACTACGGCTACACTAGAAGGACAGTATTTGGTATCTGCGCTCTGCTGAAGCCAGTTACCTTCGGAAAAA 3052

3053 GAGTTGGTAGCTCTTGATCCGGCAAACAAACCACCGCTGGTAGCGGTGGTTTTTTTGTTTGCAAGCAGCAGATTACGCGCAGAAAAAAAGGATCTCAAGA 3152

3153 AGATCCTTTGATCTTTTCTACGGGGTCTGACGCTCAGTGGAACGAAAACTCACGTTAAGGGATTTTGGTC ATG AGA TTA TCA AAA AGG ATC 3243
1 M R L S K R I 7

3244 TTC ACC TAG ATCCTTTTAAATTAAAA ATG AAG TTT TAA ATCAATCTAAAGTATAT ATG AGT AAA CTT GGT CTG ACA GTT ACC 3325
8 F T * M K F * M S K L G L T V T 9

3326 AAT GCT TAA TCAGTGAGGCACCTATCTCAGCGATCTGTCTATTTCGTTCATCCATAGTTGCCTGACTCCCCGTCGTGTAGATAACTACGATACGGGA 3422
10 N A * 12

3423 GGGCTTACCATCTGGCCCCAGTGCTGCA ATG ATA CCG CGA GAC CCA CGC TCA CCG GCT CCA GAT TTA TCA GCA ATA AAC CAG 3504
1 M I P R D P R S P A P D L S A I N Q 18

3505 CCA GCC GGA AGG GCC GAG CGC AGA AGT GGT CCT GCA ACT TTA TCC GCC TCC ATC CAG TCT ATT AAT TGT TGC CGG 3579
19 P A G R A E R R S G P A T L S A S I Q S I N C C R 43

3580 GAA GCT AGA GTA AGT AGT TCG CCA GTT AAT AGT TTG CGC AAC GTT GTT GCC ATT GCT ACA GGC ATC GTG GTG TCA 3654
44 E A R V S S S P V N S L R N V V A I A T G I V V S 68

FIG. 4B-1

```
3655 CGC TCG TCG TTT GGT ATG GCT TCA TTC AGC TCC GGT TCC CAA CGA TCA AGG CGA GTT ACA TGA TCCCCC ATG TTG 3729
  69 R   S   S   F   G   M   A   S   F   S   S   G   S   Q   R   S   R   R   V   T   *          M   L   2

3730 TGC AAA AAA GCG GTT AGC TCC TTC GGT CCT CCG ATC GTT GTC AGA AGT AAG TTG GCC GCA GTG TTA TCA CTC ATG 3804
   3 C   K   K   A   V   S   S   F   G   P   P   I   V   V   R   S   K   L   A   A   V   L   S   L   M   27

3805 GTT ATG GCA GCA CTG CAT AAT TCT CTT ACT GTC ATG CCA TCC GTA AGA TGC TTT TCT GTG ACT GGT GAG TAC TCA 3879
  28 V   M   A   A   L   H   N   S   L   T   V   M   P   S   V   R   C   F   S   V   T   G   E   Y   S   52

3880 ACC AAG TCA TTC TGA GAATAGTGT ATG CGG CGA CCG AGT TGC TCT TGC CCG GCG TCA ATA CGG GAT AAT ACC GCG 3954
  53 T   K   S   F   *             M   R   R   P   S   C   S   C   P   A   S   I   R   D   N   T   A   17

3955 CCA CAT AGC AGA ACT TTA AAA GTG CTC ATC ATT GGA AAA CGT TCT TCG GGG CGA AAA CTC TCA AGG ATC TTA CCG 4029
  18 P   H   S   R   T   L   K   V   L   I   I   G   K   R   S   S   G   R   K   L   S   R   I   L   P   42

4030 CTG TTG AGA TCC AGT TCG ATG TAA CCCACTCGTGCACCCAACTGATCTTCAGCATCTTTTACTTTCACCAGCGTTTCTGGGTGAGCAAAAAC 4121
  43 L   L   R   S   S   S   M   *                                                                                 50

4122 AGGAAGGCAAA ATG CCG CAA AAA AGG GAA TAA GGGCGACACGGAA ATG TTG AAT ACT CAT ACT CTT CCT TTT TCA ATA 4199
   1             M   P   Q   K   R   E   *                 M   L   N   T   H   T   L   P   F   S   I   11

4200 TTA TTG AAG CAT TTA TCA GGG TTA TTG TCT CAT GAG CGG ATA CAT ATT TGA ATG TAT TTA GAA AAA TAA ACAAATA 4275
  12 L   L   K   H   L   S   G   L   L   S   H   E   R   I   H   I   *   M   Y   L   E   K   *           6

4276 GGGGTTCCGCGCACATTTCCCCGAAAAGTGCCACCTGACGTCTAAGAAACCATTATTATC ATG ACA TTA ACC TAT AAA AAT AGG CGT ATC 4365
   1                                                              M   T   L   T   Y   K   N   R   R   I   10

4366 ACG AGG CCC TTT CGT CTC GCG CGT TTC GGT GAT GAC GGT GAA AAC CTC TGA CAC ATG CAG CTC CCG GAG ACG GTC 4440
  11 T   R   P   F   R   L   A   R   F   G   D   D   G   E   N   L   *       M   Q   L   P   E   T   V   7

4441 ACA GCT TGT CTG TAA GCGG ATG CCG GGA GCA GAC AAG CCC GTC AGG GCG CGT CAG CGG GTG TTG GCG GGT GTC GGG 4516
   8 T   A   C   L   *        M   P   G   A   D   K   P   V   R   A   R   Q   R   V   L   A   G   V   G   19

4517 GCT GGC TTA ACT ATG CGG CAT CAG AGC AGA TTG TAC TGA GAGTGCACCAT ATG CGG TGT GAA ATA CCG CAC AGA TGC 4593
  20 A   G   L   T   M   R   H   Q   S   R   L   Y   *               M   R   C   E   I   P   H   R   C   9

4594 GTA AGG AGA AAA TAC CGC ATC AGG CGC CAT TCG CCA TTC AGG CTG CGC AAC TGT TGG GAA GGG CGA TCG GTG CGG 4668
  10 V   R   R   K   Y   R   I   R   R   H   S   P   F   R   L   R   N   C   W   E   G   R   S   V   R   34

4669 GCC TCT TCG CTA TTA CGC CAG CTG GCG AAA GGG GGA TGT GCT GCA AGG CGA TTA AGT TGG GTA ACG CCA GGG TTT 4743
  35 A   S   S   L   L   R   Q   L   A   K   G   G   C   A   A   R   R   L   S   W   V   T   P   G   F   59

4744 TCC CAG TCA CGA CGT TGT AAA ACG ACG GCC AGT                                                         4776
  60 S   Q   S   R   R   C   K   T   T   A   S                                                           70
```

FIG. 4B-2

SEQUENCE LISTING

<160> NUMBER OF SEQ ID NOS: 34

<210> SEQ ID NO 1
<211> LENGTH: 4776
<212> TYPE: DNA
<213> ORGANISM: Murine leukemia virus

<400> SEQUENCE: 1
gaattcccgt acgagccata gataaaataa aagattttat ttagtctcca gaaaaagggg 60
ggaatgaaag accccacctg taggtttggc aagctagctt aagtaacgcc attttgcaag 120
gcatggaaaa atacataact gagaatagag aagttcagat caaggtcagg aacagatgga 180
acagctgaat atgggccaaa caggatatct gtggtaagca gttcctgccc cggctcaggg 240
ccaagaacag atggaacagc tgaatatggg ccaaacagga tatctgtggt aagcagttcc 300
tgccccggct cagggccaag aacagatggt ccccagatgc ggtccagccc tcagcagttt 360
ctagagaacc atcagatgtt tccagggtgc cccaaggacc tgaaatgacc ctgtgcctta 420
tttgaactaa ccaatcagtt cgcttctcgc ttctgttcgc gcgcttctgc tccccgagct 480
caataaaaga gcccacaacc cctcactcgg ggcgccagtc ctccgattga ctgagtcgcc 540
cgggtggggg agctcgctgt tgggctcgcg gttgaggaca aactcttcgc ggtctttcca 600
gtactcttgg atcggaaacc cgtcggcctc cgaacggtac tccgccaccg agggacctga 660
gcgagtccgc atcgaccgga tcggaaaacc tctcgagaaa ggcgtctaac cagtcacagt 720
cgcaaggtag gctgagcacc gtggccgggc ggcacgggtg gcggtcgggg ttgtttctgg 780
cggaggtgct gctgatgatg taattaagta ggcggtcttg agacggcgat ggtcgaggtg 840
aggtgtggca ggcttgagat ctggccatac acttgagtga caatgacatc cactttgcct 900
ttctctccac aggtgtccac tcccaggtcc aaccggatcc gagctccacc gcggtaaagg 960
tcgctgggaa gaccccgtgg atccaccact ctcgactcaa gaaagctcct gacaaccaag 1020
aagaatggac tgtctcacca acctccgatc cgctgagggt aaagttgacc aggcgagcaa 1080

-continued

```
aatcctaatt ctccttgtgg cttggtgggg gtttgggacc actgccgaag tttcgactgc    1140

cggctccggg ggcggtggtt ctggtggtgg ttctggtggt ggtggttctg gtggtggtgg    1200

ttctggcgcc agcccagtcc agtttatccc cctgcttgtg ggtctaggga tttcaggggc    1260

tacacttgct ggtggaacgg ggcttggggt ctccgttcac acttatcaca agctctctaa    1320

tcaattgatt gaagatgtcc aggctctttc agggaccatc aatgacctac aggaccagat    1380

tgactccctg gctgaggttg tcttacaaaa tagaagaggg ttagacctat tgactgccga    1440

acaaggagga atatgtctcg cactccagga gaagtgttgt ttttacgcta acaagtcggg    1500

tatcgtacgt gacaagatcc gaaaactcca agaggacctt atcgagagaa aacgtgcact    1560

gtacgacaac cccctgtgga gcggcttgaa cggcttcctt ccatatttgc tacccttgtt    1620

aggcccctg tttgggctca tattgttcct gaccctcggc ccgtgcatta tgaagaccct    1680

gactcgcatt atacatgaca aaattcaggc agtaaaatcc tagcactagt cccacagtac    1740

aagccactcc caacagagat ggatacccta ggggtccgat ggtctaagaa ttctcgagtc    1800

taagatcgat cgaattccta ggtcaatgat ttgaccagaa tgtacaagag cagtggggaa    1860

tgtgggaggg gcttacgaag gccttaagtg actaggtacc cgatccagac atgataagat    1920

acattgatga gtttggacaa accacaacta gaatgcagtg aaaaaaatgc tttatttgtg    1980

aaatttgtga tgctattgct ttatttgtaa ccattataag ctgcaataaa caagttaaca    2040

acaacaattg cattcatttt atgtttcagg ttcaggggga ggtgtgggag gttttttaaa    2100

gcaagtaaaa cctctacaaa tcaagctggg caagctagat ctagcttggc gtaatcatgg    2160

tcatagctgt ttcctgtgtg aaattgttat ccgctcacaa ttccacacaa catacgagcc    2220

ggaagcataa agtgtaaagc ctggggtgcc taatgagtga gctaactcac attaattgcg    2280

ttgcgctcac tgcccgcttt ccagtcggga aacctgtcgt gccagctgca ttaatgaatc    2340

ggccaacgcg cggggagagg cggtttgcgt attgggcgct cttccgcttc ctcgctcact    2400

gactcgctgc gctcggtcgt tcggctgcgg cgagcggtat cagctcactc aaaggcggta    2460

atacggttat ccacagaatc aggggataac gcaggaaaga acatgtgagc aaaaggccag    2520

caaaaggcca ggaaccgtaa aaaggccgcg ttgctggcgt ttttccatag gctccgcccc    2580

cctgacgagc atcacaaaaa tcgacgctca agtcagaggt ggcgaaaccc gacaggacta    2640

taaagatacc aggcgtttcc ccctggaagc tccctcgtgc gctctcctgt tccgaccctg    2700

ccgcttaccg gatacctgtc cgcctttctc ccttcgggaa gcgtggcgct ttctcaatgc    2760

tcacgctgta ggtatctcag ttcggtgtag gtcgttcgct ccaagctggg ctgtgtgcac    2820

gaaccccccg ttcagcccga ccgctgcgcc ttatccggta actatcgtct tgagtccaac    2880

ccggtaagac acgacttatc gccactggca gcagccactg gtaacaggat tagcagagcg    2940

aggtatgtag gcggtgctac agagttcttg aagtggtggc ctaactacgg ctacactaga    3000

aggacagtat ttggtatctg cgctctgctg aagccagtta ccttcggaaa aagagttggt    3060

agctcttgat ccggcaaaca aaccaccgct ggtagcggtg gtttttttgt ttgcaagcag    3120

cagattacgc gcagaaaaaa aggatctcaa gaagatcctt tgatcttttc tacgggtct    3180

gacgctcagt ggaacgaaaa ctcacgttaa gggattttgg tcatgagatt atcaaaaagg    3240

atcttcacct agatcctttt aaattaaaaa tgaagtttta aatcaatcta agtatatat     3300

gagtaaactt ggtctgacag ttaccaatgc ttaatcagtg aggcacctat ctcagcgatc    3360

tgtctatttc gttcatccat agttgcctga ctccccgtcg tgtagataac tacgatacgg    3420
```

-continued

```
gagggcttac catctggccc cagtgctgca atgataccgc gagacccacg ctcaccggct   3480

ccagatttat cagcaataaa ccagccagcc ggaagggccg agcgcagaag tggtcctgca   3540

actttatccg cctccatcca gtctattaat tgttgccggg aagctagagt aagtagttcg   3600

ccagttaata gtttgcgcaa cgttgttgcc attgctacag gcatcgtggt gtcacgctcg   3660

tcgtttggta tggcttcatt cagctccggt tcccaacgat caaggcgagt tacatgatcc   3720

cccatgttgt gcaaaaaagc ggttagctcc ttcggtcctc cgatcgttgt cagaagtaag   3780

ttggccgcag tgttatcact catggttatg gcagcactgc ataattctct tactgtcatg   3840

ccatccgtaa gatgcttttc tgtgactggt gagtactcaa ccaagtcatt ctgagaatag   3900

tgtatgcggc gaccgagttg ctcttgcccg gcgtcaatac gggataatac cgcgccacat   3960

agcagaactt taaaagtgct catcattgga aaacgttctt cggggcgaaa actctcaagg   4020

atcttaccgc tgttgagatc cagttcgatg taacccactc gtgcacccaa ctgatcttca   4080

gcatctttta ctttcaccag cgtttctggg tgagcaaaaa caggaaggca aaatgccgca   4140

aaaaagggaa taagggcgac acggaaatgt tgaatactca tactcttcct ttttcaatat   4200

tattgaagca tttatcaggg ttattgtctc atgagcggat acatatttga atgtatttag   4260

aaaaataaac aaataggggt tccgcgcaca tttccccgaa aagtgccacc tgacgtctaa   4320

gaaaccatta ttatcatgac attaacctat aaaaataggc gtatcacgag gccctttcgt   4380

ctcgcgcgtt tcggtgatga cggtgaaaac ctctgacaca tgcagctccc ggagacggtc   4440

acagcttgtc tgtaagcgga tgccgggagc agacaagccc gtcagggcgc gtcagcgggt   4500

gttggcgggt gtcggggctg gcttaactat gcggcatcag agcagattgt actgagagtg   4560

caccatatgc ggtgtgaaat accgcacaga tgcgtaagga gaaaataccg catcaggcgc   4620

cattcgccat tcaggctgcg caactgttgg gaagggcgat cggtgcgggc ctcttcgcta   4680

ttacgccagc tggcgaaagg gggatgtgct gcaaggcgat taagttgggt aacgccaggg   4740

ttttcccagt cacgacgttg taaaacgacg gccagt                              4776
```

```
<210> SEQ ID NO 2
<211> LENGTH: 12
<212> TYPE: PRT
<213> ORGANISM: Murine leukemia virus

<400> SEQUENCE: 2

Met Lys Asp Pro Thr Cys Arg Phe Gly Lys Leu Ala
 1               5                  10


<210> SEQ ID NO 3
<211> LENGTH: 21
<212> TYPE: PRT
<213> ORGANISM: Murine leukemia virus

<400> SEQUENCE: 3

Met Glu Lys Tyr Ile Thr Glu Asn Arg Glu Val Gln Ile Lys Val Arg
 1               5                  10                  15

Asn Arg Trp Asn Ser
            20


<210> SEQ ID NO 4
<211> LENGTH: 8
<212> TYPE: PRT
<213> ORGANISM: Murine leukemia virus

<400> SEQUENCE: 4
```

-continued

```
Met Gly Gln Thr Gly Tyr Leu Trp
 1               5


<210> SEQ ID NO 5
<211> LENGTH: 13
<212> TYPE: PRT
<213> ORGANISM: Murine leukemia virus

<400> SEQUENCE: 5

Met Glu Gln Leu Asn Met Gly Gln Thr Gly Tyr Leu Trp
 1               5                  10


<210> SEQ ID NO 6
<211> LENGTH: 12
<212> TYPE: PRT
<213> ORGANISM: Murine leukemia virus

<400> SEQUENCE: 6

Met Val Pro Arg Cys Gly Pro Ala Leu Ser Ser Phe
 1               5                  10


<210> SEQ ID NO 7
<211> LENGTH: 10
<212> TYPE: PRT
<213> ORGANISM: Murine leukemia virus

<400> SEQUENCE: 7

Met Phe Pro Gly Cys Pro Lys Asp Leu Lys
 1               5                  10


<210> SEQ ID NO 8
<211> LENGTH: 15
<212> TYPE: PRT
<213> ORGANISM: Murine leukemia virus

<400> SEQUENCE: 8

Met Val Glu Val Arg Cys Gly Arg Leu Glu Ile Trp Pro Tyr Thr
 1               5                  10                  15


<210> SEQ ID NO 9
<211> LENGTH: 24
<212> TYPE: PRT
<213> ORGANISM: Murine leukemia virus

<400> SEQUENCE: 9

Met Thr Ser Thr Leu Pro Phe Ser Pro Gln Val Ser Thr Pro Arg Ser
 1               5                  10                  15

Asn Arg Ile Arg Ala Pro Pro Arg
            20


<210> SEQ ID NO 10
<211> LENGTH: 232
<212> TYPE: PRT
<213> ORGANISM: Murine leukemia virus

<400> SEQUENCE: 10

Met Asp Cys Leu Thr Asn Leu Arg Ser Ala Glu Gly Lys Val Asp Gln
 1               5                  10                  15

Ala Ser Lys Ile Leu Ile Leu Leu Val Ala Trp Trp Gly Phe Gly Thr
            20                  25                  30

Thr Ala Glu Val Ser Thr Ala Gly Ser Gly Gly Gly Gly Ser Gly Gly
        35                  40                  45

Gly Ser Gly Gly Gly Gly Ser Gly Gly Gly Gly Ser Gly Ala Ser Pro
```

-continued

```
    50                  55                  60

Val Gln Phe Ile Pro Leu Leu Val Gly Leu Gly Ile Ser Gly Ala Thr
65                  70                  75                  80

Leu Ala Gly Gly Thr Gly Leu Gly Val Ser Val His Thr Tyr His Lys
                85                  90                  95

Leu Ser Asn Gln Leu Ile Glu Asp Val Gln Ala Leu Ser Gly Thr Ile
            100                 105                 110

Asn Asp Leu Gln Asp Gln Ile Asp Ser Leu Ala Glu Val Val Leu Gln
        115                 120                 125

Asn Arg Arg Gly Leu Asp Leu Leu Thr Ala Glu Gln Gly Gly Ile Cys
    130                 135                 140

Leu Ala Leu Gln Glu Lys Cys Cys Phe Tyr Ala Asn Lys Ser Gly Ile
145                 150                 155                 160

Val Arg Asp Lys Ile Arg Lys Leu Gln Glu Asp Leu Ile Glu Arg Lys
                165                 170                 175

Arg Ala Leu Tyr Asp Asn Pro Leu Trp Ser Gly Leu Asn Gly Phe Leu
            180                 185                 190

Pro Tyr Leu Leu Pro Leu Leu Gly Pro Leu Phe Gly Leu Ile Leu Phe
        195                 200                 205

Leu Thr Leu Gly Pro Cys Ile Met Lys Thr Leu Thr Arg Ile Ile His
    210                 215                 220

Asp Lys Ile Gln Ala Val Lys Ser
225                 230


<210> SEQ ID NO 11
<211> LENGTH: 14
<212> TYPE: PRT
<213> ORGANISM: Murine leukemia virus

<400> SEQUENCE: 11

Met Asp Thr Leu Gly Val Arg Trp Ser Lys Asn Ser Arg Val
 1               5                  10


<210> SEQ ID NO 12
<211> LENGTH: 15
<212> TYPE: PRT
<213> ORGANISM: Murine leukemia virus

<400> SEQUENCE: 12

Met Tyr Lys Ser Ser Gly Glu Cys Gly Arg Gly Leu Arg Arg Pro
 1               5                  10                  15


<210> SEQ ID NO 13
<211> LENGTH: 16
<212> TYPE: PRT
<213> ORGANISM: Murine leukemia virus

<400> SEQUENCE: 13

Met Ile Arg Tyr Ile Asp Glu Phe Gly Gln Thr Thr Thr Arg Met Gln
 1               5                  10                  15


<210> SEQ ID NO 14
<211> LENGTH: 4
<212> TYPE: PRT
<213> ORGANISM: Murine leukemia virus

<400> SEQUENCE: 14

Met Leu Tyr Leu
 1
```

-continued

<210> SEQ ID NO 15
<211> LENGTH: 6
<212> TYPE: PRT
<213> ORGANISM: Murine leukemia virus

<400> SEQUENCE: 15

Met Leu Leu Leu Tyr Leu
 1               5

<210> SEQ ID NO 16
<211> LENGTH: 12
<212> TYPE: PRT
<213> ORGANISM: Murine leukemia virus

<400> SEQUENCE: 16

Met Phe Gln Val Gln Gly Glu Val Trp Glu Val Phe
 1               5                  10

<210> SEQ ID NO 17
<211> LENGTH: 26
<212> TYPE: PRT
<213> ORGANISM: Murine leukemia virus

<400> SEQUENCE: 17

Met Val Ile Ala Val Ser Cys Val Lys Leu Leu Ser Ala His Asn Ser
 1               5                  10                  15

Thr Gln His Thr Ser Arg Lys His Lys Val
            20                  25

<210> SEQ ID NO 18
<211> LENGTH: 49
<212> TYPE: PRT
<213> ORGANISM: Murine leukemia virus

<400> SEQUENCE: 18

Met Ser Glu Leu Thr His Ile Asn Cys Val Ala Leu Thr Ala Arg Phe
 1               5                  10                  15

Pro Val Gly Lys Pro Val Val Pro Ala Ala Leu Met Asn Arg Pro Thr
            20                  25                  30

Arg Gly Glu Arg Arg Phe Ala Tyr Trp Ala Leu Phe Arg Phe Leu Ala
        35                  40                  45

His

<210> SEQ ID NO 19
<211> LENGTH: 4
<212> TYPE: PRT
<213> ORGANISM: Murine leukemia virus

<400> SEQUENCE: 19

Met Leu Thr Leu
 1

<210> SEQ ID NO 20
<211> LENGTH: 9
<212> TYPE: PRT
<213> ORGANISM: Murine leukemia virus

<400> SEQUENCE: 20

Met Arg Leu Ser Lys Arg Ile Phe Thr
 1               5

<210> SEQ ID NO 21

-continued

```
<211> LENGTH: 11
<212> TYPE: PRT
<213> ORGANISM: Murine leukemia virus

<400> SEQUENCE: 21

Met Ser Lys Leu Gly Leu Thr Val Thr Asn Ala
 1               5                  10


<210> SEQ ID NO 22
<211> LENGTH: 70
<212> TYPE: PRT
<213> ORGANISM: Murine leukemia virus

<400> SEQUENCE: 22

Met Arg Cys Glu Ile Pro His Arg Cys Val Arg Arg Lys Tyr Arg Ile
 1               5                  10                  15

Arg Arg His Ser Pro Phe Arg Leu Arg Asn Cys Trp Glu Gly Arg Ser
            20                  25                  30

Val Arg Ala Ser Ser Leu Leu Arg Gln Leu Ala Lys Gly Gly Cys Ala
        35                  40                  45

Ala Arg Arg Leu Ser Trp Val Thr Pro Gly Phe Ser Gln Ser Arg Arg
    50                  55                  60

Cys Lys Thr Thr Ala Ser
65                  70


<210> SEQ ID NO 23
<211> LENGTH: 88
<212> TYPE: PRT
<213> ORGANISM: Murine leukemia virus

<400> SEQUENCE: 23

Met Ile Pro Arg Asp Pro Arg Ser Pro Ala Pro Asp Leu Ser Ala Ile
 1               5                  10                  15

Asn Gln Pro Ala Gly Arg Ala Glu Arg Arg Ser Gly Pro Ala Thr Leu
            20                  25                  30

Ser Ala Ser Ile Gln Ser Ile Asn Cys Cys Arg Glu Ala Arg Val Ser
        35                  40                  45

Ser Ser Pro Val Asn Ser Leu Arg Asn Val Val Ala Ile Ala Thr Gly
    50                  55                  60

Ile Val Val Ser Arg Ser Ser Phe Gly Met Ala Ser Phe Ser Ser Gly
65                  70                  75                  80

Ser Gln Arg Ser Arg Arg Val Thr
                85


<210> SEQ ID NO 24
<211> LENGTH: 56
<212> TYPE: PRT
<213> ORGANISM: Murine leukemia virus

<400> SEQUENCE: 24

Met Leu Cys Lys Lys Ala Val Ser Ser Phe Gly Pro Pro Ile Val Val
 1               5                  10                  15

Arg Ser Lys Leu Ala Ala Val Leu Ser Leu Met Val Met Ala Ala Leu
            20                  25                  30

His Asn Ser Leu Thr Val Met Pro Ser Val Arg Cys Phe Ser Val Thr
        35                  40                  45

Gly Glu Tyr Ser Thr Lys Ser Phe
    50                  55
```

-continued

<210> SEQ ID NO 25
<211> LENGTH: 49
<212> TYPE: PRT
<213> ORGANISM: Murine leukemia virus

<400> SEQUENCE: 25

```
Met Arg Arg Pro Ser Cys Ser Cys Pro Ala Ser Ile Arg Asp Asn Thr
 1               5                  10                  15

Ala Pro His Ser Arg Thr Leu Lys Val Leu Ile Ile Gly Lys Arg Ser
            20                  25                  30

Ser Gly Arg Lys Leu Ser Arg Ile Leu Pro Leu Leu Arg Ser Ser Ser
        35                  40                  45

Met
```

<210> SEQ ID NO 26
<211> LENGTH: 6
<212> TYPE: PRT
<213> ORGANISM: Murine leukemia virus

<400> SEQUENCE: 26

```
Met Pro Gln Lys Arg Glu
 1               5
```

<210> SEQ ID NO 27
<211> LENGTH: 27
<212> TYPE: PRT
<213> ORGANISM: Murine leukemia virus

<400> SEQUENCE: 27

```
Met Leu Asn Thr His Thr Leu Pro Phe Ser Ile Leu Leu Lys His Leu
 1               5                  10                  15

Ser Gly Leu Leu Ser His Glu Arg Ile His Ile
            20                  25
```

<210> SEQ ID NO 28
<211> LENGTH: 5
<212> TYPE: PRT
<213> ORGANISM: Murine leukemia virus

<400> SEQUENCE: 28

```
Met Tyr Leu Glu Lys
 1               5
```

<210> SEQ ID NO 29
<211> LENGTH: 26
<212> TYPE: PRT
<213> ORGANISM: Murine leukemia virus

<400> SEQUENCE: 29

```
Met Thr Leu Thr Tyr Lys Asn Arg Arg Ile Thr Arg Pro Phe Arg Leu
 1               5                  10                  15

Ala Arg Phe Gly Asp Asp Gly Glu Asn Leu
            20                  25
```

<210> SEQ ID NO 30
<211> LENGTH: 11
<212> TYPE: PRT
<213> ORGANISM: Murine leukemia virus

<400> SEQUENCE: 30

```
Met Gln Leu Pro Glu Thr Val Thr Ala Cys Leu
 1               5                  10
```

-continued

```
<210> SEQ ID NO 31
<211> LENGTH: 31
<212> TYPE: PRT
<213> ORGANISM: Murine leukemia virus

<400> SEQUENCE: 31

Met Pro Gly Ala Asp Lys Pro Val Arg Ala Arg Gln Arg Val Leu Ala
 1               5                  10                  15

Gly Val Gly Ala Gly Leu Thr Met Arg His Gln Ser Arg Leu Tyr
            20                  25                  30


<210> SEQ ID NO 32
<211> LENGTH: 51
<212> TYPE: DNA
<213> ORGANISM: Artificial Sequence
<220> FEATURE:
<223> OTHER INFORMATION: oligonucleotide for PCR

<400> SEQUENCE: 32

gggccctcgc gagcggccca gccggccgac atcaagatga cccagtctcc a             51


<210> SEQ ID NO 33
<211> LENGTH: 45
<212> TYPE: DNA
<213> ORGANISM: Artificial Sequence
<220> FEATURE:
<223> OTHER INFORMATION: oligonucleotide for PCR

<400> SEQUENCE: 33

gggccctcgc gatgcggccg ctgaggagac tgtgagagtg gtgcc                    45


<210> SEQ ID NO 34
<211> LENGTH: 16
<212> TYPE: PRT
<213> ORGANISM: Artificial Sequence
<220> FEATURE:
<223> OTHER INFORMATION: polypeptide

<400> SEQUENCE: 34

Ser Gly Gly Gly Gly Ser Gly Gly Gly Gly Ser Gly Gly Gly Gly Gly
 1               5                  10                  15
```

PSEUDO-TYPE RETROVIRAL VECTORS WITH MODIFIABLE SURFACE CAPSID PROTEINS

FIELD OF THE INVENTION

The present invention relates to retroviral pseudo-type vectors having modified surface envelope proteins suitable for cell specific transduction of a selected mammalian cell type (cell targeting), methods for the preparation of the cell-specific retroviral pseudo-type vectors and their use for gene transfer into selected cells.

BACKGROUND OF THE INVENTION

The aim of somatic gene therapy is the effective transfer of genes or gene fragments with functional homology to a defective gene or of genes or gene fragments with therapeutic effects. Previous experiments and clinical studies of somatic gene therapy have been conducted predominantly on the basis of retroviral murine leukemia viruses (MLV). The host cell region of retroviral vectors is determined by the surface envelope protein (SU) encoded by the env gene. The protein products of the env gene form the outer envelope of the retroviral vector. The SU proteins interact with, ie, bind to, a specific protein (receptor) on the surface of the host cell. The env gene products of, for example, amphotropic MLV enable gene transfer into a great number of different mammalian cells. Generally, both ecotropic and amphotropic MLV vectors transduce all murine (ecotropic) and murine and human cells (amphotropic), respectively, since the receptors targeted by these viruses are ubiquitous. Accordingly, cell-specific gene transfer by means of MLV is not possible.

Host cell specificity, however, is advantageous e.g. for the use in gene therapy since in a gene therapy outside of the organism (ex vivo) (Anderson et al., Science 256 (1992) 808–813; Yu et al., H. Gene Therapy 8 (1997) 1065–1072) laborious purifications of cells may be avoided. For therapeutic, diagnostic or vaccination use in vivo it is desirable to specifically target the retroviral vectors to the desired host cells which are affected by genetic malfunctions or are the therapy target, respectively, and subsequently transfer the therapeutic gene.

A restriction of the host cell range of e.g. the amphotropic MLV has been achieved by modification of the surface envelope protein. One modification of the surface envelope protein has been carried out by fusion to a hormone domain. Transduction of the cells carrying the specific hormone receptor occurred (Kasahara et al., Science 266 (1994) 1373–1375). Further, the surface envelope protein was modified by fusion to a single chain antibody fragment (single chain variable fragment, in the following also referred to as "scFv"). The fragment represented the antigen binding domain of an antibody and is a fusion protein composed of the variable domains $V_H$ and $V_L$ of a monoclonal antibody. Both domains are linked via a glycine and serine oligopeptide [-(ser-gly4)3-gly-)] which enables correct folding of the fusion protein (Huston et al., Methods Enzymol. 203 (1991) 46–88, Whitlow et al., Methods: A companion to Methods Enzymol. 2 (1991) 97–105). All modifications of the MLV surface envelope protein using an scFv carried out so far showed that while binding of the vectors to the host target cell occurred, however, they failed to enter the cell (Russel et al., Nucleic Acid Res. 21 (1993) 1081–1085). Furthermore it is known that the surface envelope protein of the MLV generally does not allow extensive modifications (Cosset et al., J. Virol. 69 (1995) 6314–632). Modifications in which a portion of the binding domain of the MLV-SU protein has been replaced led to incorrect processing and, thus, to defects in transport of the SU protein to the cell surface (Weiss et al., In J. A. Levy (ed.) The Retroviridae 2 (1993) 1–108; Morgan et al., J. Virol 67 (1993) 4712–4721; Russel et al., Nucleic Acids Res. 21 (1993) 1081–1085).

To avoid the problem of necessary modification of the surface envelope protein required for the specific targeting of the desired cell type, the preparation of host cell-specific retroviral vectors has been achieved by pseudotyping of for example MLV envelopes. In this case the viral core is derived from MLV and the viral envelope (SU proteins) is derived from other retroviral vectors. The advantages of pseudotyping of MLV capsids are that the risk of replication-competent retroviruses which might arise is minimized. By using different non-homologous expression plasmids encoding the structural genes gag, pol, and env the risk of recombination is reduced. In this manner it has been shown that MLV capsids having ENV proteins of the simian sarcoma associated virus (Takeuschi et al., Virology 186 (1992) 792–794), the feline leukemia virus (Porter et al., Hum. Gene Ther. 7 (1996) 913–919) and of feline endogenous retroviruses (Vile et al., Virology 180 (1991) 420–424), respectively, may be pseudo typed. Reiser et al. (Proc. Natl. Acad. Sci. USA 93 (1996) 15266–15271) were able to demonstrate the possibility of preparation of HIV/MLV and HIV/VSV-G pseudo-types, respectively. Similarly, the possible incorporation of VSV-G protein (Burns et al., Proc. Natl. Acad. Sci. USA 90 (1993) 8033–8037; Ory et al., Proc. Natl. Acad. Sci. USA 93 (1996) 11400–11406) as well as the incorporation of truncated HIV env glycoproteins (Schnierle et al., Proc. Natl. Acad. Sci. USA 94 (1997) 8640–8645) has been described. The vectors pseudo typed in this way, however, are unable to target any desired cell-specific receptor of a cell type since the target cell is determined only by the tropism (cell-specificity of a virus) of the respective viral surface protein.

SUMMARY OF THE INVENTION

Generally, gene transfer into mammalian cells by means of (pseudo typed retroviruses) retroviral vectors has following benefits:

- Normally, one copy of the desired gene is transferred into the mammalian cell.
- Generally, the desired gene is transferred without mutation or rearrangements.
- A stable incorporation of the desired gene into the genome of the target cell occurs.

Furthermore, gene transfer into mammalian cells using pseudo-typed retroviruses has the advantage that by means of pseudo typing e.g. MLV, HIV, foamy virus, or SIV capsids mainly with SNV-ENV protein a specific alteration in cell specificity of the respective retroviral vectors may be achieved so that for example a therapeutical gene may be introduced into a selected cell population.

Therefore, it is an object of the present invention to provide retroviral pseudo type vectors having modified surface envelope proteins suitable for cell-specific transduction of a selected mammalian cell type (cell targeting). Further, it is an object of the present invention to provide a method for the preparation of said cell-specific retroviral pseudo type vectors. Moreover, it is an object of the present invention to provide retroviral packaging cells for obtaining the vectors according to the present invention. In contrast to vectors known up to now, using these vectors it is possible to target any desired receptor of a target cell.

The object of the present invention has been solved by the retroviral vectors of the present invention comprising viral cores of e.g. murine leukemia virus (MLV), human immunodeficiency virus (HIV), simian immunodeficiency virus (SIV), or foamy virus as well as viral capsids of spleen necrosis virus (SNV). Preferred vectors are retroviral vectors in which the viral envelopes comprise the full length surface protein (SU protein) of SNV and/or a chimeric SNV-non-viral polypeptide-ENV, SNV-HIV-ENV or SNV-SIV-ENV. Particularly preferred are retroviral vectors in which the non-viral polypeptide comprises a ligand, a peptide fragment of a ligand, an antibody, a peptide fragment of an antibody or an antibody recognition domain (scFv). Further preferred are retroviral vectors which further comprise an RNA to be introduced into the cell which is to be transduced by the retroviral vector. Particularly preferred are retroviral vectors in which the RNA comprises a therapeutic gene or a nucleic acid fragment of a therapeutic gene and/or a reporter gene. Especially preferred are retroviral vectors wherein the therapeutic gene or the nucleic acid fragment of a therapeutic gene comprises the CFTR gene, phox91, ADA, IL-16, p53, transdominant mutants (e.g. revM10) as well as vaccination genes, e.g. recombinant gp120 and IL-16. Further particularly preferred are retroviral vectors wherein the reporter gene comprises β-galactosidase, "green fluorescent protein", luciferase or the resistance genes neomycin or "multiple drug resistance gene". The retroviral vectors according to the present invention may be used as medicaments. The use in the preparation of a medicament for somatic gene therapy, vaccination therapy or diagnostics is preferred. Particularly preferred is the therapy of cystic fibrosis, ADA deficiency, chronic granulomatosis, and HIV infection.

Furthermore, the object of the present invention has been solved by the retroviral packaging cells according to the invention for obtaining the retroviral vectors of the invention. The retroviral packaging cells according to the present invention are transformed both with one or more psi-negative expression construct(s) expressing the gag and pol gene products of MLV, HIV, SWV, or foamy virus, and with a psi-negative SNV-Env and/or psi-negative SNV-Env-non-viral polypeptide, psi-negative SNV-HIV-ENV or SNV-SIV-env expression construct. A retroviral packaging cell is preferred in which the non-viral polypeptide of the psi-negative SNV-Env-non-viral polypeptide expression construct comprises a ligand, a peptide fragment: of a ligand, an antibody, a peptide fragment of an antibody or an antibody recognition domain (scFv). Further preferred is a retroviral packaging cell line further comprising a psi-positive expression construct comprising a nucleic acid sequence to be introduced into the cell to be transduced by the retroviral vector. Especially preferred is a retroviral packaging cell line, wherein the nucleic acid sequence comprises a therapeutic gene or its nucleic acid fragment and/or a reporter gene. Particularly preferred is a retroviral packaging cell line wherein the therapeutic gene or the nucleic acid fragment of a therapeutic gene comprises the CFTR gene, phox91, ADA, IL-16, p53, transdominant mutations (e.g. revM10), and vaccination genes, e.g. recombinant gp120 and IL-16. Further particularly preferred is a retroviral packaging cell line wherein the reporter gene comprises β-galactosidase, "green fluorescent protein", luciferase or the resistance genes neomycin or the "multiple drug resistance gene".

Other features and advantages of the invention will be apparent from the following detailed description, and from the claims.

BRIEF DESCRIPTION OF THE DRAWINGS

The figures are meant to illustrate the invention.

FIG. 4 shows the nucleic acid sequence of pTC53.

DETAILED DESCRIPTION

Figure 1:
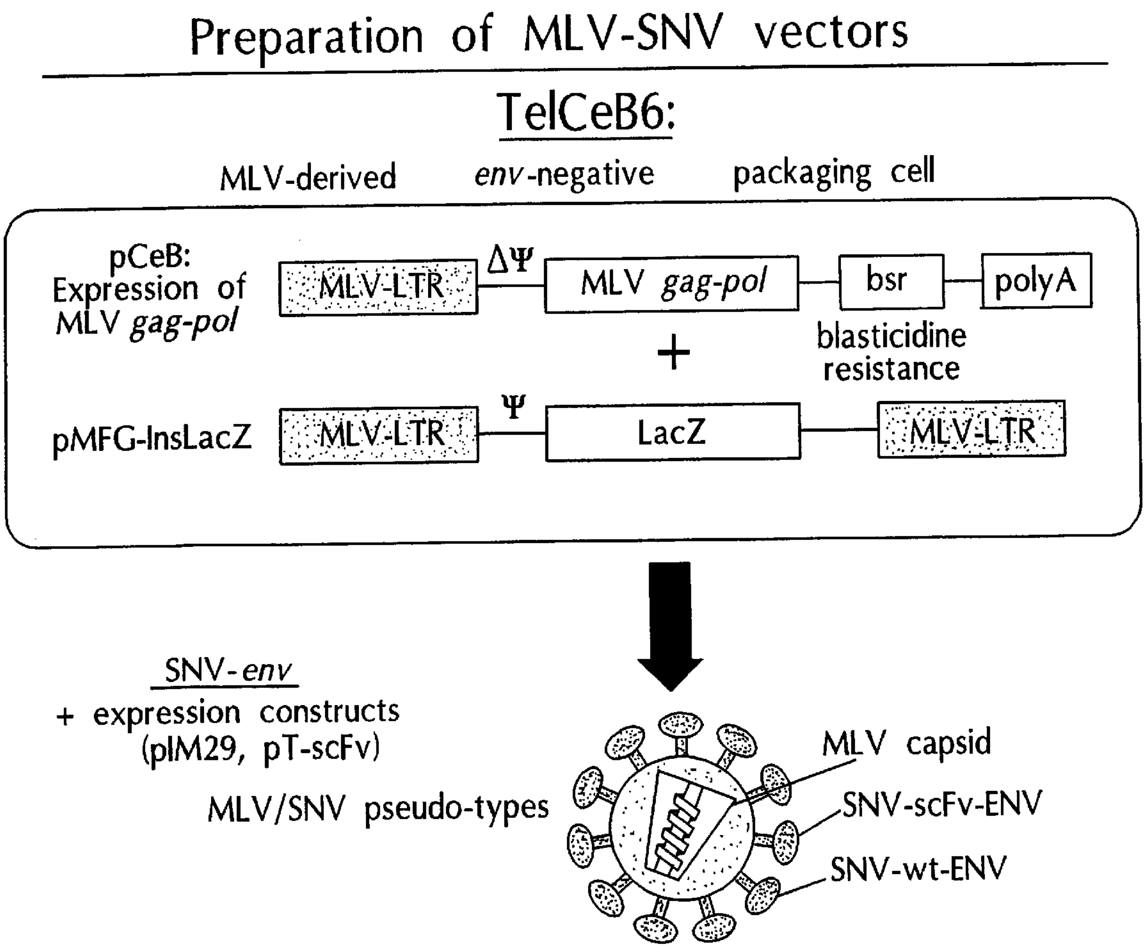
FIG. 1 is a schematic depiction of the preparation of an MLV/SNV pseudo type vector. The packaging cell line TelCeB6 contains the constructs pCeB and pMFG-InsLacZ. Thus, the cell expresses the structural genes gag and pol as well as the β-galactosidase reporter gene. For the preparation of a pseudo typed vector the SNV-env expression constructs (see FIG. 2) are transfected into the cell. By this, also the structural genes for the wt env (pIM29; Chu et al., 1997) and the chimeric scFv-env (pT-scFv) are provided and expressed. Vector particles composed of MLV envelopes and incorporating SNV-env proteins into their viral capsids are released into the cell culture supernatant. Packaged in the MLV envelope is only the pMFG-InsLacZ RNA enabling detection the reporter gene of this gene product after successful gene transfer (transduction of the target cells).
Figure 2:
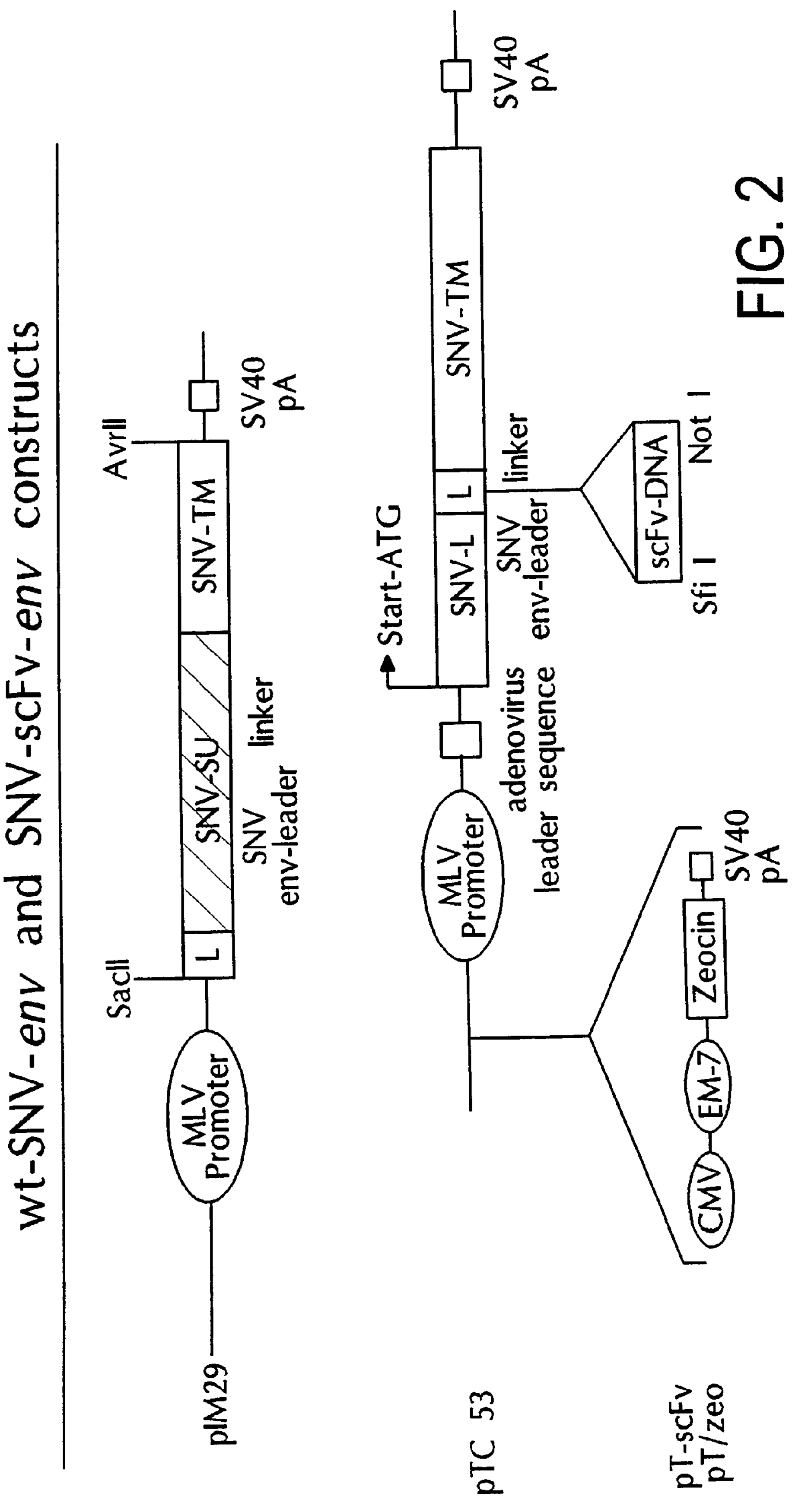
FIG. 2 is a schematic depiction of construct pIM29 encoding the SNV-wt-env gene as well as the chimeric SNV-scFv-env gene constructs.
Figure 3:
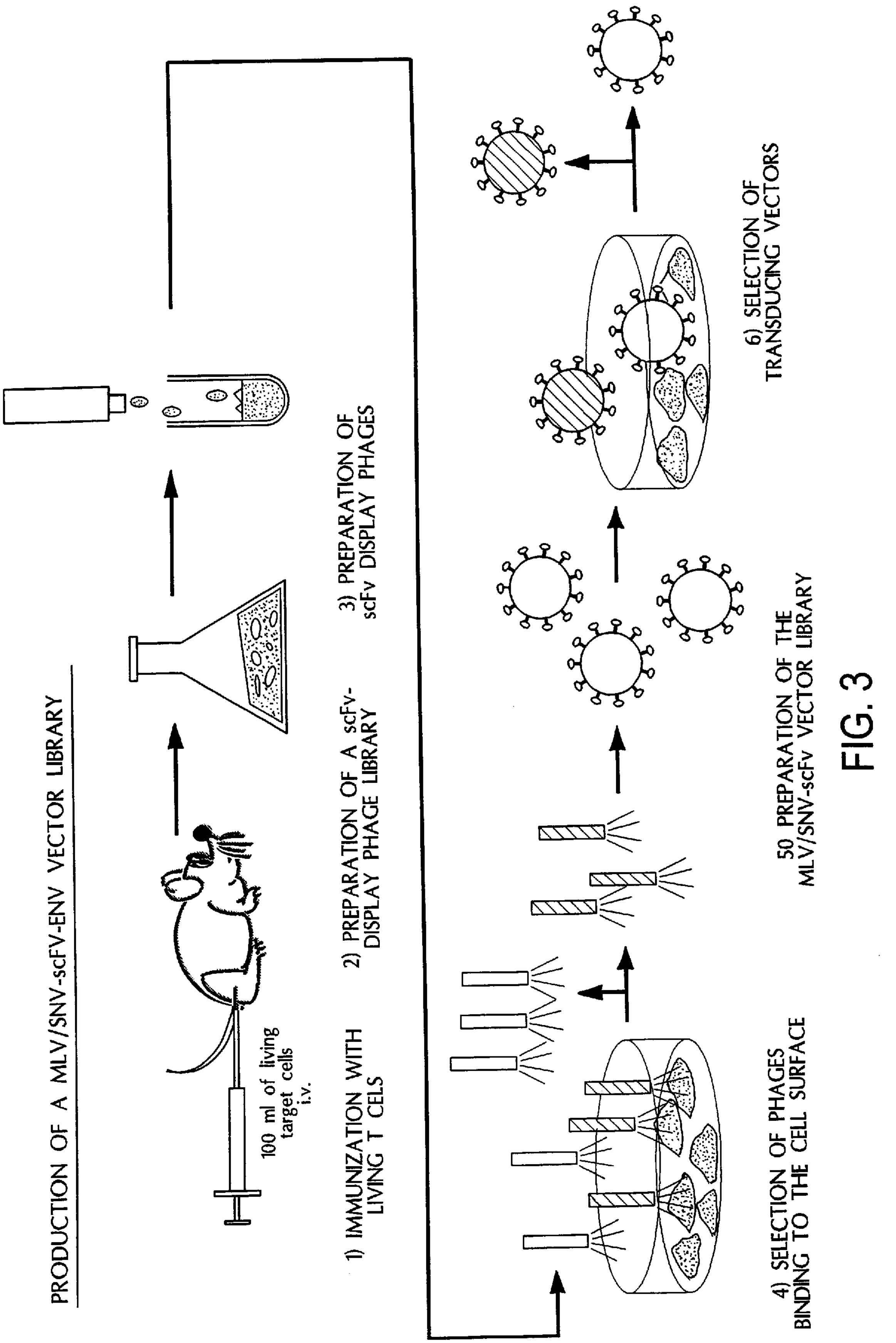
FIG. 3 is a schematic depiction of the preparation, isolation, and selection for the vectors of the present invention.

The term amphotropic virus used herein means infection and replication in murine and human cells in contrast to ecotropic viruses which replicate only in murine cells. The term retroviral vector used herein means replication-deficient retroviral virus particle which instead of retroviral mRNA may transmit a foreign introduced RNA of a gene, e.g. of a therapeutic gene or a fragment thereof or of a reporter gene. The term pseudo typed used herein means that the retroviral vector has a virus core of a retrovirus and that its virus envelope is derived from another virus. The term antibody recognition domain (scFV) used herein means antigen binding site of an antibody comprising a Vh and Vl chain.

To provide the pseudo typed retroviral vector according to the present invention, first, an expression construct is prepared comprising the GAG and POL gene products of for example MLV, HIV, SIV, or foamy virus. The expression construct is psi-negative, i.e. the packaging signal (Ψ) has been deleted. In this way, the expression construct encoding the gag and pol genes, e.g. pCeB (Cosset et al., J. Virol. 69 (1995) 6314–632) is not packaged into the nascent retroviral vectors so that an non-replication competent virus is prepared. The SNV env gene is an additional component. By modification of the surface envelope protein (SU protein), for example by insertion of an antibody, antibody fragment, scFvs or a ligand of a surface receptor of e.g. human cells or other non-viral polypeptides the original tropism of SNV (avian cells) may be altered. In contrast to the surface protein of MLV which tolerates only moderate modification (Weiss et al., In J. A. Levy (ed.) The Retroviridae 2 (1993) 1–108; Morgan et al., J. Virol. 67 (1993) 4712–4721; Russel et al., Nucleic Acid Res. 21 (1993) 1081–1085) the SNV surface protein may be completely substituted by a non-viral polypeptide without affecting the processing of e.g. a chimeric SNV-scFv-ENV protein (Martinez and Dornburg, 1994; Chu and Dornburg, J. Virol, 71 (1997) 720–725). The non-viral polypeptides, for example the scFv domains, of the surface envelope protein mediate recognition and binding to surface proteins of selected cell populations, e.g. of hematopoietic cells, T-cells, liver cells, epithelial cells, muscle cells, or fibroblasts of for example man, mouse, rat, sheep, or cattle. For efficient transduction of the selected cells, also the wild type SNV-ENV proteins may be incorporated in addition to the modified ENV proteins into the MLV envelopes. Also the plasmid encoding the wild type SNV-ENV protein must be psi-negative in order to avoid incorporation of the corresponding messenger RNA into retroviral particles. For example, the HIV/SNV and foamy virus/SNV pseudo types, respectively, according to the present invention are suitable for gene transfer into resting differentiated cells (Naldini et al., Science 272 (1996) 263–267; Lindemann et al., J. Virol. 71 (1997) 48715–4820).

Another expression construct contains a DNA sequence of the gene product to be introduced into the cell to be transduced by the pseudo typed retroviral vector. The DNA sequence may be a therapeutic gene, a gene fragment of a therapeutic gene, a DNA fragment of a gene mutated in the target cell, or a marker gene. Typical examples of a DNA sequence are the CFTR gene, ADA gene, LDL receptor gene, β-globin gene, Factor VIII gene or Factor IX gene or the dystrophin gene. In the case of the CFTR gene the target cells of the vector according to the present invention would be e.g. the lung epithelial cells, for the ADA gene the bone marrow stem cells or T lymphocytes, for LDL receptor the liver cells, for the dystrophin gene the skeletal muscle cells, for the β globin gene the hematopoietic stem cells, for factor VIII or factor IX the and liver cells. It is obvious to the skilled artisan that this listing represents only a selection of the therapeutic genes and that other genes may also be transfected into the packaging cell line of the present invention for packaging into the vectors of the present invention. The DNA fragments of a therapeutic gene comprise for example antisense nucleic acids or ribozymes. Furthermore, DNA fragments of a gene mutated in the target cell may comprise regions of a gene comprising the trinucleotide repeats of e.g. the fragile X gene. A marker gene or reporter gene is for example β-galactosidase, “green fluorescent protein”, luciferase or the neomycin resistance gene. The preparation of such expression constructs is known from the prior art, for example the expression construct MFG-InsLacZ derived from MLV contains the cDNA for the β-galactosidase reporter gene (Takeuchi et al., J. Virol. 68 (1994) 8001–8007). Packaging of this expression plasmid into the retroviral vector must be ensured to effect gene transfer. Therefore, the presence of a packaging site (psi, Ψ) is typical for such an expression construct.

The construction of gag and pol expression constructs for MLV, HIV, SIV, foamy virus is known from the prior art (Naldini et al., Science 272 (1996) 263–267; Ory, D. S., Proc. Natl. Acad. Sci. USA 93 (1996) 11400–11406; Poeschla et al., Proc. Natl. Acad. Sci. USA 93 (1996) 11395–11399; Buchschacher et al., J. Virol. 66 (1992) 2731–2739; Poznansky et al., 1991; Mammano et al., J. Virol. 71 (1997) 3341–3345).

The construction of expression plasmids encoding wt-SNV-ENV proteins, e.g. pIM29, and the chimeric SNV-scFv-ENV proteins has been described previously by Chu et al. (J. Virol. 71 (1997) 720–725). The expression of the DNA encoding the wt-env gene is controlled by an MLV promoter. The env cDNA has been excised from the plasmid coding for the complete SNV virus using the SacII and AvrII restriction sites and incorporated into a linker (L) by insertion. To ensure correct processing of the protein, pIM 29 contains the simian virus 40 (SV40) polyadenylation site. Thus, the wt-env gene may be expressed from this plasmid in a way that proteolytic cleavage of a precursor protein yields the outer glycoprotein (SU) and the transmembrane protein (TM). However, also other plasmids, promoters, linkers, polyadenylation signals and other DNA elements required for correct processing known to the skilled artisan may be used.

For expression of SNV-scFv-ENV proteins, the scFv obtained in the known way may be introduced into an SNV-ENV expression construct such as pTC53 in a usual manner. The restriction recognition sites present in pTC53 for the enzymes SfiI and NotI enable molecular cloning of for example scFvs between the SNV-env leader sequence and the DNA region encoding the transmembrane protein (TM). The protease cleavage site located between SU and TM of not-ENV has been deleted from pTC53 leading to expression of a fusion protein consisting, at its N terminus, of the single-chain antibody fragment and, at its C terminus, of SNV-TM.

The regulatory elements, such as MLV promoter and SV40 polyadenylation signal are identical to those of the pIM29 vector. For enhancing the expression of a chimeric env gene a adenoviral leader sequence such as AVtl (Sheay et al. BioTechniques 15 (1993) 856–861) is inserted into expression plasmid pTC53. A zeozine cassette (pSV2zeo; Invitrogen Corp., The Netherlands) may function to possibly select stably transfected cells so that single cell clones may be established.

Any antibody recognition domains specific for any desired target cell may be produced by preparing a combinatorial phage cDNA library of the variable domains of the immunoglobulin light and heavy chains. For this purpose, a mammal, e.g. a mouse, rat, rabbit, guinea pig, goat, or sheep is immunized with a sufficient titer of a cell population in a usual manner. The cell population is the cell type forming a surface receptor to which the scFv specifically bind. The cells may be derived from a mammal which is different from the mammal to be immunized, e.g. from human, mouse, rat, sheep, cattle, or pig. The cells may be such cells in which for example a gene therapy, a vaccination therapy, or diagnostics have to be carried out. For immunization, a cell population or several all populations may be simultaneously administered to the mammal depending on the cell populations for which the retroviral vector is to be specific.

For the preparation of the cDNA library, first, B cell RNA of the immunized mammal is isolated in a known manner. The mRNA sequences of the regions of the immunoglobulin heavy and light chain ($V_H$ and $V_L$) responsible for antigen recognition are transcribed into cDNA and amplified in a usual manner by means of reverse transcription and subsequent polymerase chain amplification. The primer pairs and their sequences for the $V_H$ and $V_L$ regions are known to the person skilled in the art. For example, they are contained in the kit commercially available of Pharmacia company or may be derived from known data bases (EMBL), respectively. It is known to the skilled artisan that he has to use different primer sequences for each immunized mammalian species. The sequences are also contained in the known data bases. Then, the cDNA fragments of the $V_H$ and $V_L$ regions are linked to scFv cDNAs by means of a ligase reaction in a usual manner. It is obvious to the skilled artisan that different combinations of cDNA fragments are prepared during ligation. The resulting scFv cDNAs may then be cloned into a phagemid vector, e.g. pCANTA 5E phagemid of Pharmacia company. Subsequently, host bacteria such as *E. coli* TGl are transformed with the phagemid vector.

The recombinant phages produced by the bacteria are then isolated in a usual manner and selected for the presence of cell-specific scFv peptides. The phages are then contacted in a usual manner with the cell population(s) used for immunization. Phages which do not bind to the cells do not carry a specific scFv peptide and are removed by means of washing steps in a usual manner. Phages which bind to the cells present the desired scFv peptide on their surface and are eluted in a usual manner. Phages presenting the desired scFv peptide are amplified by allowing them to infect host bacteria in a usual manner. This selection step may be repeated once or several times to enrich the phages which bind: This procedure is referred to as "panning". After panning or directly after the first selection step, the phages are subjected to further selection. For this purpose, the phages are contacted with one or more other cell populations different from the cells used for immunization. Phages not binding to said cells present a cell-specific scFv peptide. They are isolated from the cell supernatant in a conventional manner and are used for infection of host bacteria for amplification. Also this selection step may be repeated once or several times (Marks et al., Biotechnologie 10 (1992) 779; Clackson et al., Nature 352 (1991) 624; Marks et al,, J. Mol. Biol. 222 (1991) 581; Chaudhary et al., Proc. Natl. Acad. Sci USA 87 (1990) 1066; Chiswell et al., TIBTECH 10 (1992) 80; McCafferty et al., Nature 348 (1990) 552; Huston et al., Proc. Natl. Acad. Sci. USA 85 (1988) 5879).

The phages selected in the manner described above are used as a starting material for the preparation of a vector gene library for the pseudo-typed retroviral vectors according to the present invention. Thus, each vector of the type [MLV/SNV-scFv-ENV] contains in its envelope a particular scFv domain. Then, those pseudo-typed retroviral vectors were chosen from the vector gene library which may perform gene transfer into the target cells selected, i.e. the cells which had been used for immunization of the mammal. For this purpose, individual [MLV/SNV-scFv-ENV] vectors with a single scFv in their envelope or pools of such vectors were prepared and tested with respect to their ability to transduce genes into the selected cells. Only those vectors and, thus, the scFv used in the preparation of these vectors were chosen in the manner described above which carry out the targeted gene transfer into the selected target cells.

Moreover, the SNV surface protein may be replaced not only by non-viral polypeptides but also by the external glycoprotein (SIVagm) of the simian immunodeficiency virus (SIV) of the African vervet monkey (Cercopithecus aethiops) or the HIV-1 or HIV-2 ENV protein. Such chimeric SNV/SIV ENV proteins or SNV/HIV ENV proteins, respectively, may also be incorporated into the MLV capsids in the manner described above. These pseudo-typed retroviral vectors according to the present invention may be used in cell-specific gene transfer into CD4-positive lymphocytes.

The retroviral packaging cell line of the present invention for obtaining the pseudo-typed retroviral vectors according to the invention is provided by transfecting a cell line such as a human cell line with the psi-negative expression constructs described above expressing the gag and pol gene products of MLV, HIV, SIV, or foamy virus, and with the psi-negative SNV-Env expression construct and/or psi-negative SNV Env-non-viral polypeptide expression construct, SNV/HIV or SNV/SIV expression construct in a usual manner.

Furthermore, packaging cells may be used which already contain the psi-negative expression constructs for the gag and pol gene products. A typical example for an MLV-derived packaging cell of this type is TelCeB6 (Cosset et al., J. Virol. 69 (1995) 6314–632). Into such packaging cells, only the psi-negative expression construct for the viral capsid and the psi-positive expression construct for the nucleic acid sequence to be transduced into the target cell have to be transfected. Methods for transfection of the expression constructs are known to those skilled in the art. By the packaging cells according to the invention, retroviral vector particles are released into the supernatant containing the expression construct but lacking the constructs encoding the GAG, POL, and ENV proteins. Therefore, only the desired gene, e.g. the therapeutic gene or reporter gene, is introduced into the target cell. Up to now, the targeted transduction of selected target cells, for example by means of SNV/SNV-scFv-Env vectors was only demonstrated using different scFvs (Chu et al, Gene Therapy 1 (1994) 292–299; Chu et al., BioTechniques 18 (1995) 890–899). To establish a stable packaging cell line, a zeozin construct is introduced and the packaging cells are selected in the usual manner.

Establishing stable packaging cell lines which stably express both the wt-SNV ENV and chimeric SNV ENV, SNV/HIV ENV or SNV/SIV ENV expression constructs enables the generation of high titer vector stocks. These are desirable for specific cell targeting.

The illustrated invention opens up the following possibilities:

Genes, gene fragments or other nucleic acid sequences may be transferred into selected mammalian cells, further enhancement of the efficiency of the nucleic acid transfer may be achieved by improvement of the env gene constructs, gene therapy, labeling and vaccination strategies may be developed for which a selective nucleic acid transfer into selected mammalian cells is desirable.

The following examples illustrate the invention and should not be construed as limiting:

1. Isolation and Cloning of Cell-specific scFvs

For the preparation, isolation and selection of cell-specific scFvs a mouse was immunized with the human T cell line T-C8166 (Clapham et al., Virology 158 (1987) 44–51) in a conventional manner, the spleen removed and the RNA was isolated. Cloning of the scFv cDNAs was carried out using the kit commercially available from Pharmacia company according to the manufacturer's instructions. The resulting phages were examined in a conventional manner with respect to their binding characteristics to target cells.

2. Cloning of Specific scFv cDNA Fragments into Env Expression Constructs

Four cell-specific scFvs (M8, K6, 7A5, 7E10) obtained in this way were used for the preparation of pseudo typed MLV-SNV-scFv vectors. The scFv cDNAs of the cell-specific scFvs described above were excised in the usual manner from the phagemid DNA and ligated into the expression construct pTC53. pTC53 was obtained by modification of the universal eukaryotic vector pRD114 (Chu et al., J. Virol. 71 (1997) 720–725; Sheay et al. BioTechniques 15 (1993) 856–861; Chu et al., BioTechniques 18 (1995) 890–895). In this vector, the SNV-wt env gene was deleted except for the leader sequence and the cDNA encoding the transmembrane protein. A spacer inserted additionally enables the insertion of a foreign DNA (here the scFv-cDNA) following the ENV-leader sequence via the NaeI restriction recognition site. The sequence of pTC53 is shown in FIG. 4. For insertion of the scFv cDNA the Env expression construct pTC53 was modified so that Sfi I and Not I specific restriction endonuclease recognition sites are inserted between the SNV leader sequence and the SNV transmembrane sequence (TM) in a usual manner. For this purpose, a recombinant PCR is carried out in a usual manner using DNA of plasmid PKA1558 (Scov, H. & Andersen, K. B., 1993) and the DNA coding for the anti-transferrin receptor scFv as starting materials so that the amplified fragment may be inserted into Nae I restricted pTC53 via Nru I (5' and 3'). The fragment inserted in this way contains the multiple Sfi I/Not I cloning site since the primers used include a Sfi I or Not I recognition site, respectively, in the neighborhood of the terminal Nru I recognition site. The following primers were used for recombinant PCR:

PKATFNNRu+:
5'-GGGCCCTCGCGAGC
GGCCCAGCCGGCCGACATCAAGATGACCCAGTC
TCCA-3' Nru I Sfi I

PKATFNRNRu−:
5'-GGGCCCTCGCGAT
GCGGCCGCTGAGGAGACTGTGAGAGTGGTGCC-3'
Nru I Not I

The PCR conditions were: 94° C./3 min, 94° C./1 min, 59° C./1 min, 72° C./1 min., 25 cycles, 72° C./10 min and then cooling to 4° C. The PCR fragment was separated by gel electrophoresis, extracted from the gel matrix (Quiaex, Quiagen company) and ligated to plasmid pTC53 opened by Nae I in a conventional manner.

The scFv-cDNAs from the phagemid (pCANTA 5E) were excised by means of restriction endonucleases Sfi I and Not I. For this purpose, the phagemid plasmid DNA was prepared by means of known methods, and 8 μg of plaid DNA were digested with 60 U each of restriction endonucleases Sfi I and Not I at 50° C. for 1.5 h and subsequently at 37° C. for 1.5 h. The reaction batch had a volume of 200 μl which was supplemented with 20 μl of BSA (10×conc.) and 20 μl reaction puffer 3 (10×conc.). Upon completion of the reaction period the batch was separated by gel electrophoresis on a 1% agarose gel. Following separation, the band specific for the scFv cDNA (about 750 bp) was purified from the agarose gel by means of known methods.

The purified fragment was ligated to the Env expression construct pTC53 which had also been opened by restriction endonucleases Sfi I and Not I. For this purpose, equimolar amounts of the scFv cDNA fragment and pTC53 fragment in a volume of 15 μl were supplemented with 200 U T4 ligase and 1.5 μl of 10×ligase buffer. The batch was incubated at 4° C. overnight. To enable an efficient transformation of bacteria, the bacterial strains TOP10F' and JS5 were made competent by means of a modified method according to Hanahan (1983). Following inoculation of 100 ml LB medium with 500 μl of an overnight culture, the bacterial suspension was incubated at 37° C. up to a density ($OD_{550}$) of 0.6. Subsequently, the bacteria were chilled on ice, pelleted at 6000 rpm and 4° C. (Minifuge RF, Heraeus, Hanau) and resuspended in 40 ml buffer TFB1 (30 mM KOAc, 100 mM $RbCl_2$, 10 mM $CaCl_2$, 15% glycerol, pH 5.8, adjusted with acetic acid, afterwards filter-sterilized). After an incubation period of 15 min on ice and centrifugation at 6000 rpm and 4° C. the bacterial pellet was resuspended in 4 ml buffer TFB2 (10 mM MOPS, 75 mM $CaCl_2$, 10 mM $RbCl_2$, 15% glycerol, pH-Wert 6.5, adjusted with KOH solution, afterwards filter-sterilized). The bacterial suspension was then divided into aliquots of 100 μl each and shock frozen on dry ice. The storage was carried out at −70° C. For transformation, 100 μl of competent bacteria were thawed on ice, and, following addition of 1–2 μl of the respective ligation batch incubated on ice for 30 min. After a subsequent temperature shock (45 s at 42° C., afterwards 2 min on ice) the bacteria were added with 500 μl SOC medium (GIBCO/BRL, Eggenstein) and cultured at 37° C. for 1 h in a bacteria shaker for expression of the antibiotic resistance. The bacterial suspension was streaked out on LB agar plates supplemented with the antibiotic ampicillin and incubated at 37° C. overnight.

The preparation of plasmids from bacteria (*E. coli* TopF10) was done using the QIAGEN plasmid kits of QIAGEN company, Hilden. For the preparation of a low amount of plasmid DNA the bacteria of a 15 ml overnight culture (LB medium with 50 μg/ml ampicillin) were lysed with the solutions provided by the manufacturer and purified via an anion exchange column (tip-20). For the preparation of large amounts of plasmid DNA (maxi preparation) 400 ml overnight cultures were prepared.

2. Transfection of Packaging Cells

First, it was tested whether incorporation of the wt SNV ENV protein into the MLV capsids occurs. For this purpose, 2 μg DNA of expression construct pIM29 (Dornburg, Gene Therapy 2 (1995) 1–10) encoding the wt ENV protein was introduced into the TelCeB6 packaging cells using a liposome-mediated gene transfer technique (lipofection). The DNA was solubilized in medium (DMEM) in a total volume of 100 μl. 2.5 μl of Lipofectamin (Gibco company, Eggenstein) were also solubilized in a total volume of 100 μl medium. Both solutions were mixed and incubated at room temperature for 30 min to enable formation of liposome-DNA complexes. Afterwards, 800 μl medium were added and the solution was added to the cells to be transfected. The cells were incubated in an incubator for four hours at 37° C. and 5% $CO_2$, followed by a medium change (DMEM, 10% FCS, NSP). The transfected cells were incubated for further 3 days at 37° C. and 5% $CO_2$ to allow for expression of the wild type env gene. No medium change was carried out during this period.

3. Transduction of Target Cells Using Different MLV/SNV Vectors

Three days after transfection, the cell supernatant of the transfected cells was harvested in a usual manner and filtered (0.45 μm filter) to remove all of the packaging cells. Two ml of this cell-free cell supernatant was employed in the transduction of $2\times10^5$ cells of the canine osteosarcoma cell line D17 (Watanabe and Temin, Mol. Cell Biol. 3 (1983) 2241–2249) in usual manner. While the cells are SNV-permissive, the natural receptor targeted by SNV is unknown up to now. The transduction was performed in the presence of 40 μg/ml polybrene for 4 hours. Subsequently, the cells were washed twice with 3 ml PBS and a medium change was carried out. To test for successful transduction, an X-gal test according to the method of Sanes et al. (1986) was carried out after 72 hours. The cell culture supernatant was removed and the cells were washed with PBS without ($Ca^{2+}$ and $Mg^{2+}$). Afterwards, the cells were overlaid with fixing solution (2% formaldehyde, 0.2% glutaraldehyde in PBS) for 5 min and washed with PBS. Then, the cells were resuspended in 3 ml of X-gal reaction mix solution (1 mg/ml, 5 mM K ferric cyanide, 5 mM K ferrous cyanide, 2 mM $MgCl_2$). After incubation of the sample for 4 hours at 37° C. blue staining of the transduced cells occurred. The blue color indicates β-galactosidase expression which only takes place if the MFG-nesLacZ expression construct has been successfully transferred into the target cells. To determine the vector titer each of 10 visual fields of cells were monitored for blue cells under the microscope. The average number of blue cells per visual field was extrapolated to the total area of the cell culture flask (6 well plate of Nunc company, Wiesbaden, 962 $mm^2$) and normalized to one ml of cell culture supernatant. The titer achieved in this transient test was $2\times10^4$ vector particles/ml cell culture supernatant.

4. Transduction of Target Cells Using Different MLV/SNV-scFv Vectors

By co-transfection of 2 μg DNA each of SNV-scFv expression constructs and 2 μg DNA of plasmid pIM29 encoding the wild type ENV protein into TelCeB6 packaging cells it was tested whether a targeted gene transfer is possible by means of different MLV/SNV vectors carrying antibody recognition fragments. The expression constructs used, pTC53-7A5zeo, pTC53-M8zeo, pTC53-K6-2zeo, and pTC53-7E10zeo each contained scFvs directed against therefore non-defined receptors of the lymphoid cell line C8166 (Clapham et al., Virology 158 (1987) 44–51). The constructs mentioned are SNV-scFv-ENV expression plasmids of the scFvs obtained in Example 1. The CD4-positive cell lines C8166 and Molt4/8 were transduced by the method described in Example 3 using cell-free supernatants. By transduction of the [MLV/SNV pTC53-7E10zeo] pseudo type a titer of $5\times10^3$ vector particles/ml cell culture supernatant could be achieved in C8166 cells, while in HeLa cells (epithelial cell line) no gene transfer was detected in the X-gal test. Thus, a cell-specific transduction had occurred. Also for the transduction of the four MLV-SNV-scFv pseudo-types into Molt4/8 cells described above, a titer of $5\times10^3$ vector particles/ml cell culture supernatant could be achieved.

5. Establishment of Stable Packaging Cell Lines

First, an MLV-derived packaging cell line was prepared which stably expresses the wt SNV ENV protein, For this purpose, expression construct pIM29 (2 μg of DNA) and construct pREP4 expressing hygromycin (0.1 μg of DNA) (Invitrogen, Belgium) are co-transfected into the TelCeB6 packaging cell line. The experimental procedure is described under 2. Three days after transfection, the transfected cells are seeded in different concentrations (1/10, 3/10, and 5/10 of the total volume) onto three culture plates. The cells are incubated for 24 hours, followed by a medium change (DMEM, 10% FCS, 200 μg/ml hygromycin). Cells which are not hygromycin-resistant detached from the cell culture flask so that individual resistant cell colonies could be obtained. These cell clones were expanded and then tested for the presence of the wt SNV ENV protein in a transduction of D17 target cells. The cell line TelCeB6-pIM29-hygro established in this manner may be employed in the transduction of another expression construct. Transfection of the chimeric SNV-scFv-ENV is carried out in a manner analogous to the method described above. For selection of a cell clone stably expressing the chimeric SNV-scFv-ENV, however, G418-containing DMEM medium is used since the chimeric env constructs contain the neomycin resistance gene.

What is claimed is:

1. A retroviral vector comprising:

(a) a viral core comprising a murine leukemia virus (MLV) viral core; and (b) a viral envelope comprising a spleen necrosis virus (SNV) capsid protein.

2. The vector of claim 1, wherein the capsid protein comprises an SNV surface protein (SU protein).

3. The vector of claim 1, further comprising an RNA molecule that is introduced into a cell when the cell is transduced by the vector.

4. The vector of claim 3, wherein the RNA molecule is a transcript of a gene.

5. The vector of claim 4, wherein the gene is selected from the group consisting of a cystic fibrosis transmembrane conductance regulator (CFTR) gene, a phox91 gene, an adenosine dearninase (ADA) gene, an interleukin-16 (IL-16) gene, a p53 gene, a revM10 gene, a gp120 gene, or fragments thereof.

6. A composition comprising the vector of claim 1 and a pharmaceutically acceptable carrier.

7. The vector of claim 3, wherein the RNA molecule is a fragment of a gene.

8. The vector of claim 4, wherein the gene is a reporter gene.

9. The vector of claim 8, wherein the reporter gene encodes β-galactosidase, green fluorescent protein, or luciferase.

10. The vector of claim 4, wherein the gene is a drug resistance gene.

11. The vector of claim 10, wherein the drug resistance gene confers resistance to neomycin or is the multiple drug resistance (mdr) gene.

* * * * *

UNITED STATES PATENT AND TRADEMARK OFFICE

CERTIFICATE OF CORRECTION

PATENT NO. : 6,544,779 B1 
DATED : April 8, 2003
INVENTOR(S) : Heike Merget-Millitzer and Klaus Cichutek It is certified that error appears in the above-identified patent and that said Letters Patent is hereby corrected as shown below:

Title page,
Item [30], Foreign Application Priority Data, insert -- .4 -- after "197 52 855."
Item [56], References Cited, OTHER PUBLICATIONS,
"Mammano et al.," insert -- s -- after "Allow."

Column 27,
Line 61, delete "dearninase" replace with -- deaminase --.

Signed and Sealed this

Twenty-seventh Day of January, 2004

JON W. DUDAS
*Acting Director of the United States Patent and Trademark Office*